(12) United States Patent
Crepel et al.

(10) Patent No.: US 10,016,424 B2
(45) Date of Patent: Jul. 10, 2018

(54) METHOD AND PHARMACEUTICAL COMPOSITION FOR USE IN THE TREATMENT OF EPILEPSY

(71) Applicants: INSERM (Institut National de la Sante et de la Recherche Medicale), Paris (FR); Universite d'Aix Marseille, Marseilles (FR); Centre National de la Recherche Scientifique (CNRS), Paris (FR); UNIVERSITE DE BORDEAUX, Bordeaux (FR)

(72) Inventors: Valerie Crepel, Marseilles (FR); Christophe Mulle, Bordeaux (FR); Angelique Peret, Marseilles (FR)

(73) Assignees: INSERM (INSTITUT NATIONAL DE LA SANTÉ ET DE LA RECHERCHE MÉDICALE, Paris (FR); UNIVERSITÉ D'AIX MARSEILLE, Marseilles (FR); CENTRE NATIONAL DE LA RECHERCHE SCIENTIFIQUE (CNRS), Paris (FR); UNIVERSITE DE BORDEAUX, Bordeaux (FR)

( * ) Notice: Subject to any disclaimer, the term of this patent is extended or adjusted under 35 U.S.C. 154(b) by 0 days.

(21) Appl. No.: 15/021,802

(22) PCT Filed: Sep. 16, 2014

(86) PCT No.: PCT/EP2014/069709
§ 371 (c)(1),
(2) Date: Mar. 14, 2016

(87) PCT Pub. No.: WO2015/036618
PCT Pub. Date: Mar. 19, 2015

(65) Prior Publication Data
US 2016/0228439 A1    Aug. 11, 2016

(30) Foreign Application Priority Data

Sep. 16, 2013 (EP) ..................................... 13306265

(51) Int. Cl.
A61K 31/505 (2006.01)
A61K 31/513 (2006.01)
A61K 31/381 (2006.01)

(52) U.S. Cl.
CPC .......... *A61K 31/513* (2013.01); *A61K 31/381* (2013.01)

(58) Field of Classification Search
CPC ........................... A61K 31/513; A61K 31/381
USPC ......................................................... 514/274
See application file for complete search history.

(56) References Cited

U.S. PATENT DOCUMENTS 4,975,430 A    12/1990 Jahr et al.

FOREIGN PATENT DOCUMENTS

WO    01/72709 A1    10/2001

OTHER PUBLICATIONS

Pinheiro et al.; "Selective Block of Postsynaptic Kainate Receptors Reveals Their Function at Hippocampal Mossy Fiber Synapses"; Cerebral Cortex, vol. 23, No. 2, Feb. 1, 2013, pp. 323-331.
Jane et al.; "Kainate receptors: Pharmacology, function and therapeutic potential"; Neuropharmacology, vol. 56, No. 1, Jan. 1, 2009, pp. 90-113.
Nilsen et al.; "Characterization of the Tetanus Toxin Model of Refractory Focal Neocoritcal Epilepsy in the Rat"; Epilepsia, vol. 46, No. 2, Feb. 2005, pp. 179-187.
Namba et al.; "Antiepileptogenic and anticonvulsant effects of NBQX, a selective AMPA receptor antagonist, in the rat kindling model of epilepsy"; Brain Research, vol. 638, No. 1-2, Feb. 28, 1994, pp. 36-44.
Pinheiro et al.; "Kainate receptors"; Cell and Tissue Research, vol. 326, No. 2, Nov. 2006, pp. 458-482.
Larsen et al.,; "Medicinal Chemistry of Competitive Kainate Receptor Anatagonists"; ACS Chemical Neuroscience, vol. 2, No. 2, Feb. 16, 2011, pp. 60-74.

*Primary Examiner* — Kevin E Weddington
(74) *Attorney, Agent, or Firm* — W&C IP

(57) ABSTRACT

The present invention relates to a compound which is an antagonist of the GluK2/GluK5 receptor or an inhibitor of the GluK2/GluK5 receptor expression for use in the treatment or the prevention of epilepsy.

3 Claims, 5 Drawing Sheets

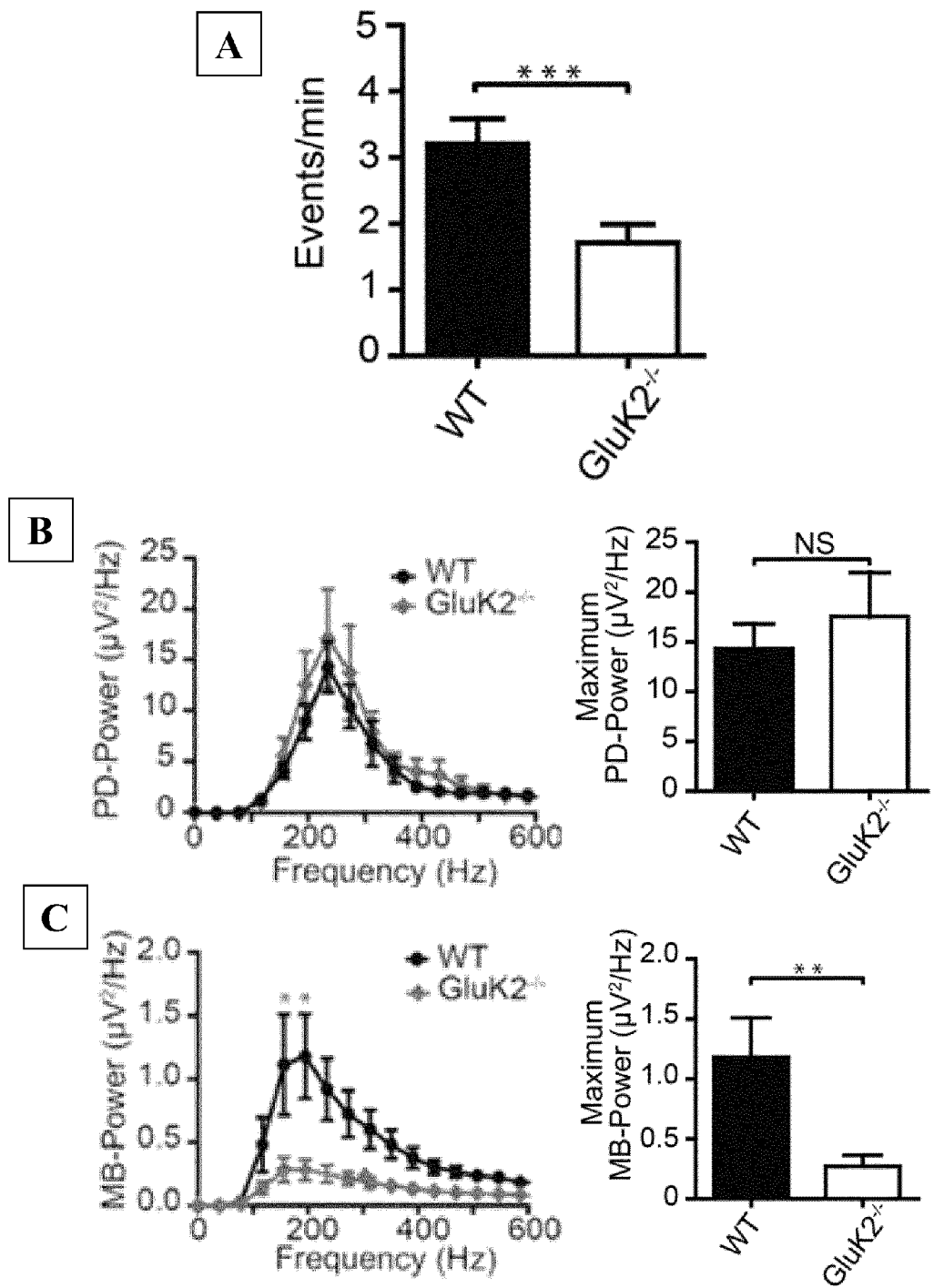
Figure 1 A, B and C

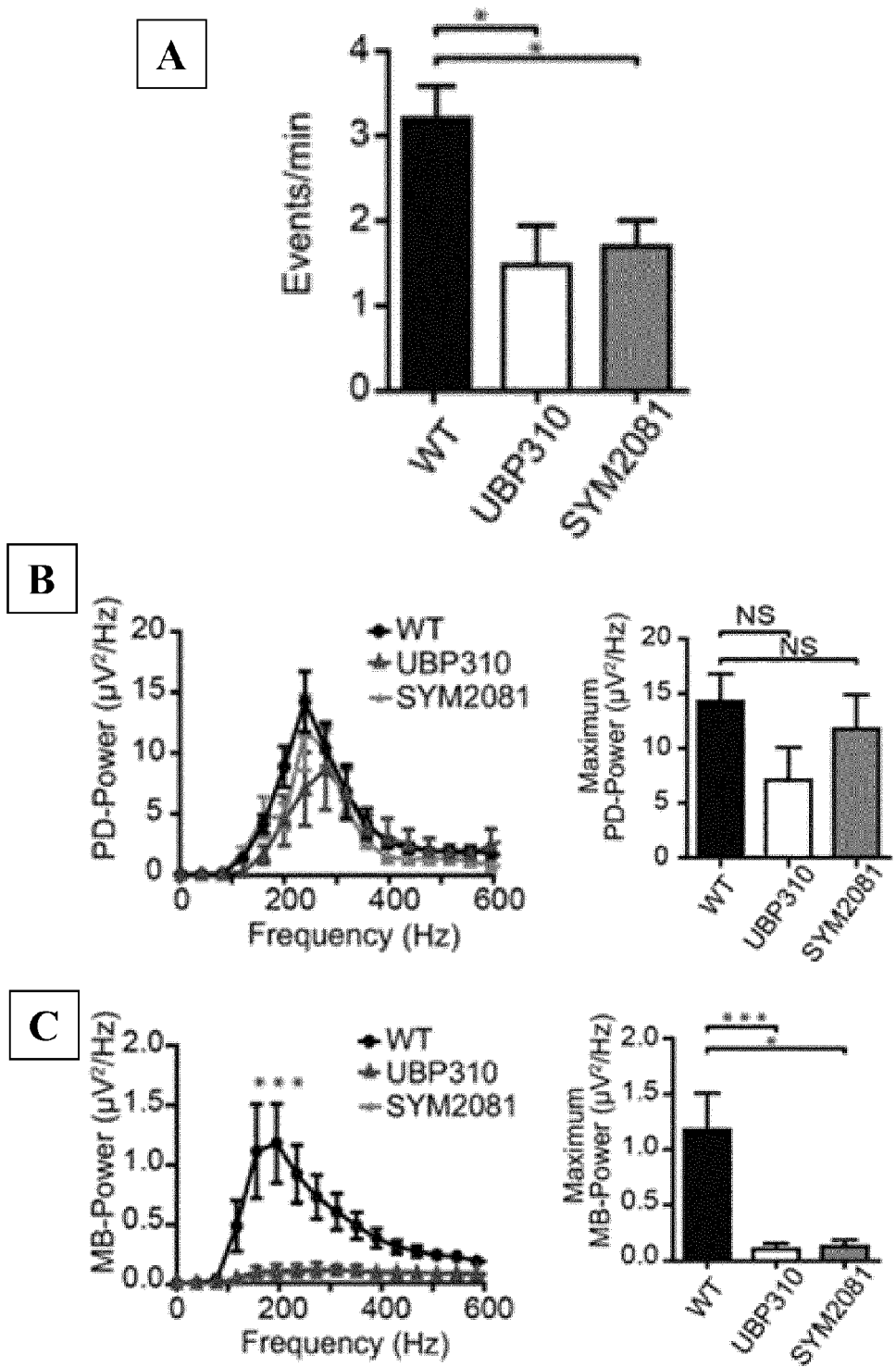
Figure 2 A, B and C

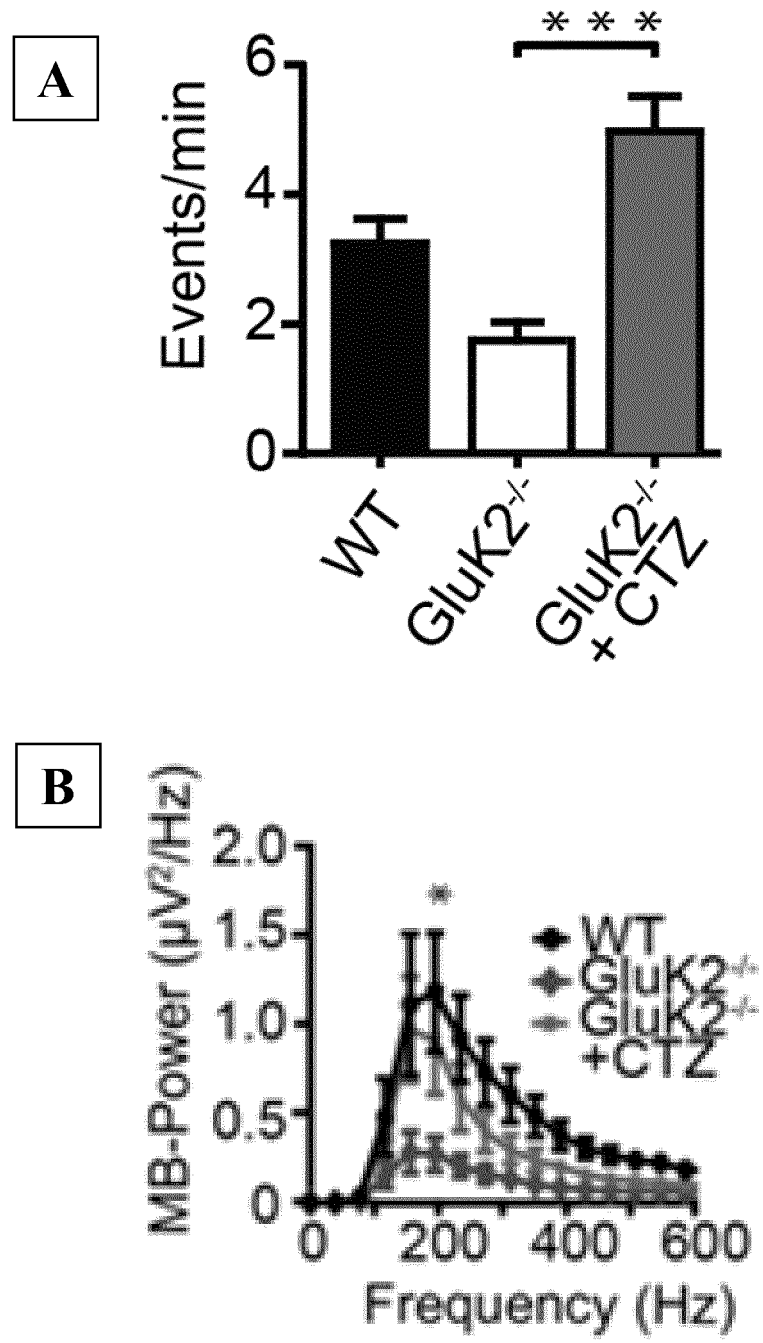
Figure 3 A and B

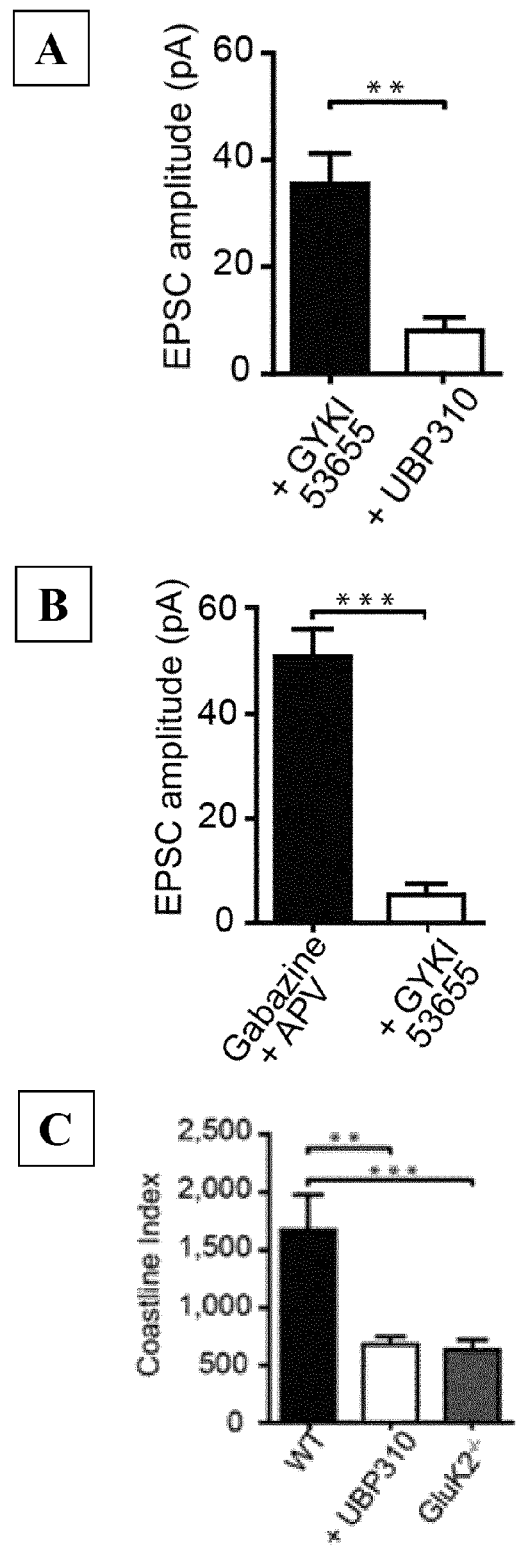
Figure 4 A, B and C

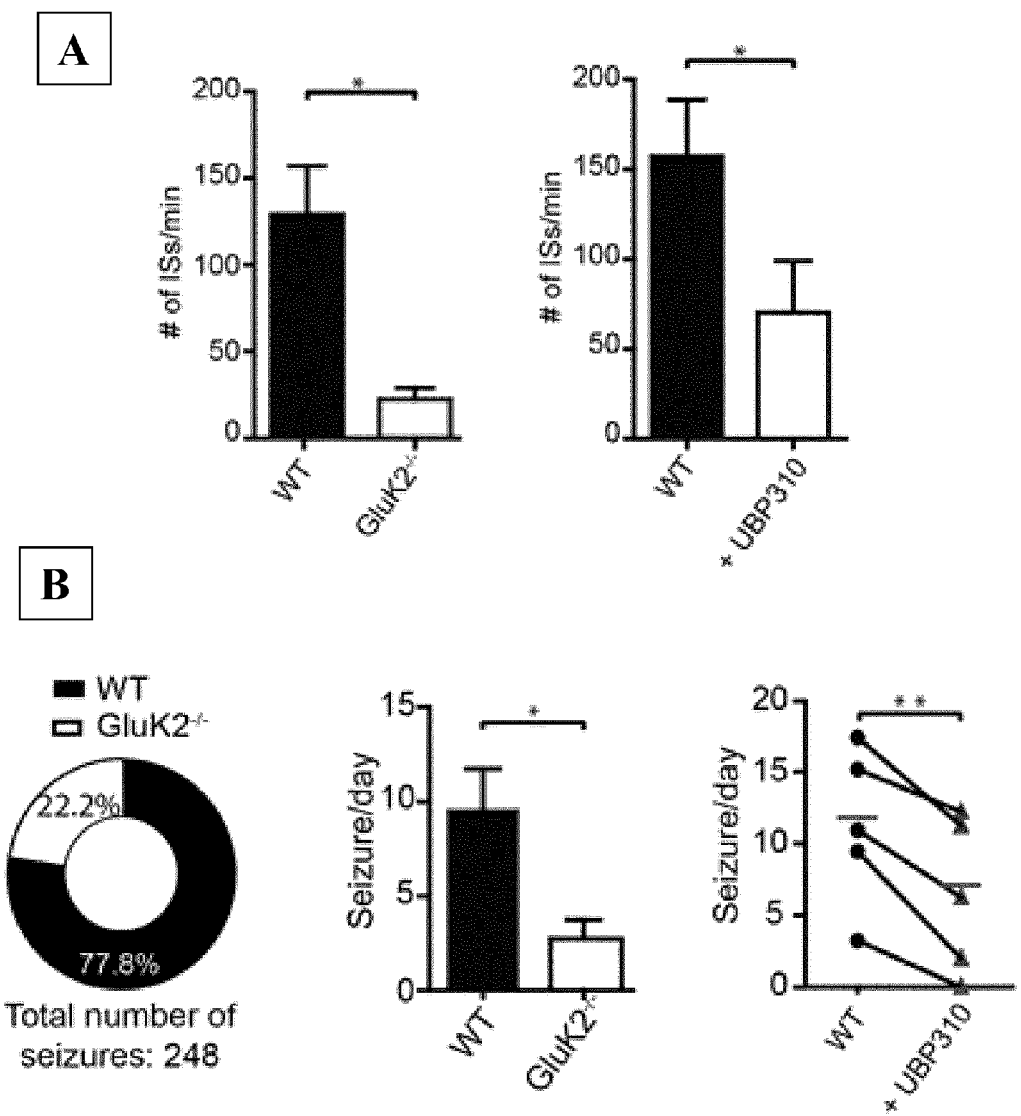
Figure 5 A and B

METHOD AND PHARMACEUTICAL COMPOSITION FOR USE IN THE TREATMENT OF EPILEPSY

FIELD OF THE INVENTION

The present invention relates to a compound which is an antagonist of the GluK2/GluK5 receptor or an inhibitor of the GluK2/GluK5 receptor expression for use in the treatment or the prevention of epilepsy.

BACKGROUND OF THE INVENTION

Epilepsy is a common and diverse set of chronic neurological disorders characterized by seizures. Some definitions of epilepsy require that seizures be recurrent and unprovoked, but others require only a single seizure combined with brain alterations which increase the chance of future seizures. In many cases a cause cannot be identified; however, factors that are associated include brain trauma, strokes, brain cancer, and drug and alcohol misuse among others.

Epileptic seizures result from abnormal, excessive or hypersynchronous neuronal activity in the brain. About 50 million people worldwide have epilepsy, and nearly 80% of epilepsy occurs in developing countries. Epilepsy becomes more common as people age. Onset of new cases occurs most frequently in infants and the elderly. As a consequence of brain surgery, epileptic seizures may occur in recovering patients.

Epilepsy is usually controlled, but not cured, with medication. However, more than 30% of people with epilepsy do not have seizure control even with the best available medications. Surgery may be considered in difficult cases.

Accordingly, there is a need to develop new drugs that will be suitable for preventing or treating epilepsy and especially chronic epilepsy. In this way, it has been suggested that characterization of new therapeutic compounds in epilepsy may be highly desirable.

Kainate (KA), an analogue of glutamate, is a potent neurotoxin that has long been known to induce behavioral and electrophysiological acute seizures reminiscent of those found in patients with temporal lobe epilepsy (TLE). However, whether kainate receptors (KARs) activated by the endogenous agonist glutamate play any role in the chronic phase of TLE was yet unknown until Jul. 24, 2014 (the inventors has published the data of the present invention; Peret et al. 2014), although this could represent a promising therapeutic approach. In animal models of TLE and in human patients, neuronal tissue undergoes major reorganization. Sprouting of hippocampal mossy fibers is one of the best documented examples of seizure-triggered reactive plasticity in human patients and animal models of TLE [Represa et al., 1989a; Represa et al., 1989b, Sutula et al., 1989; Mello et al., 1993; Isokawa et al., 1993; Franck et al., 1995; Okazaki et al., 1995; Gabriel et al., 2004;]. This sprouting leads to the formation of powerful recurrent excitatory circuits between dentate granule cells (DGCs), which accounts for, in part, the enhanced ability of the hippocampus to generate epileptiform activity in the hippocampus of human patients and animal models of TLE [Tauck and Nadler, 1985; Mello et al., 1993; Patrylo and Dudek, 1998; Lynch and Sutula, 2000; Buckmaster et al., 2002; Scharfman et al., 2003; Gabriel et al., 2004]. In addition to axonal rewiring, mossy fiber sprouting triggers the recruitment of kainate receptors (KARs) at the aberrant recurrent excitatory synapses in DGCs. Indeed, inputs impinging on DGCs operate mostly via aberrant KARs and drive synaptic events with abnormal long lasting kinetics not present in naïve conditions [Epsztein et al., 2005; Epsztein et al., 2010; Artinian et al., 2011]. In keeping with this, an increased density of kainate binding sites was previously reported in the DG of epileptic patients [Represa et al., 1989b].

State of art, already shows the implication of GluK1 and GluK2 receptors and the potential use of antagonists of these KARs in acute seizures (induced by convulsive chemical agents) in naïve animals [see for example Jane et al., 2009]. However, experiments disclosed in this state of art only relate to cases of acute seizures; these set of experiments have not addressed chronic epilepsy and notably the morpho-functional re-organisation of neuronal networks not present in naïve animals and the sprouting of hippocampal mossy fibers. This re-organisation is only present when chronic epilepsy is installed (i.e. weeks after the initial status epilepticus induced by one injection of convulsive chemical agent like kainate or pilocarpine) and thus not just after one application of the convulsive agents in naïve tissue. More, until Jul. 24, 2014 (the inventors has published the data of the present invention; Peret et al. 2014), the state of the art did not unveil the role of kainate receptors in chronic epileptic conditions.

SUMMARY OF THE INVENTION

The inventors explore the pathophysiological implications of KARs in animal models during the chronic phase of TLE through the use of KAR-subunit deficient mice and selected pharmacological agents. They show using the pilocarpine-status epilepticus model of chronic TLE, that in mice lacking the GluK2 subunit ($GluK2^{-/-}$), there is a strong reduction of both recurrent and spontaneous interictal and ictal activities in the dentate gyrus (DG) recorded in vitro and in vivo in chronic epileptic conditions. These results are fully corroborated by the use of UBP310, an antagonist of heteromeric GluK2/GluK5 receptors. This compound was initially designed as a GluK1 antagonist, but the authors have shown that this agent also blocks postsynaptic KARs and inhibits GluK2/GluK5, but not homomeric GluK2 receptors. Therefore, they show that heteromeric GluK2/GluK5 receptors and homomeric GluK2 receptors are distinct receptors with different pharmacological properties. In addition, UBP310 does not interfere with normal synaptic transmission due to the AMPA receptor [Pinheiro et al, 2013]. Therefore and contrary to the state of art which only discloses the potential interest of GluK2, GluA2 or mGluR5 receptors in epilepsy (see for example the patent applications WO01/72709, WO02/092086 or WO2007/101116), they demonstrate for the first time that KARs, and notably the heteromeric GluK2/GluK5 receptors, play a major role in epileptic activities in the hippocampus in TLE and can constitute a major antiepileptic target to treat chronic epilepsy.

Thus, the present invention relates to a compound which is an antagonist of the GluK2/GluK5 receptor or an inhibitor of the GluK2/GluK5 receptor expression for use in the treatment or the prevention of epilepsy.

DETAILED DESCRIPTION OF THE INVENTION

A first object of the invention relates to a compound which is an antagonist of the GluK2/GluK5 receptor or an inhibitor of the GluK2/GluK5 receptor expression for use in the treatment or the prevention of epilepsy.

As used herein, the term "GluK2/GluK5 receptor" denotes a heteromeric complex formed by the kainate receptor subunits GluK2 and GluK5 [see for example Reiner et al., 2012]. As used herein, the IUPHAR-2009-term "GluK2" (also known as GluR6) and IUPHAR-2009-term "GluK5" (also known as KA2,) denotes 2 different subunits of the ionotropic glutamate receptor family which bind kainate.

As used herein, the term "antagonist of the GluK2/GluK5 receptor" denotes a compound which prevents the activation of the pathway receptor or a compound which prevent the formation of the heteromeric complex GluK2/GluK5. Thus, the compound of the invention may be a molecule which binds to the GluK2/GluK5 receptor to prevent the activation or the formation of the heteromeric complex GluK2/GluK5.

In one embodiment, the invention relates to a compound which prevents the activation or the formation of the heteromeric complex GluK2/GluK5 for use in the treatment of epilepsy.

In a particular embodiment, the compound of the invention binds to GluK2 subunit or GluK5 subunit.

In a particular embodiment, the compound of the invention binds to the heteromeric GluK2/GluK5 receptor.

In another particular embodiment, the compound of the invention binds to the GluK2a or the GluK2b subunit.

In another particular embodiment, the compound of the invention binds to the domains formed from the non-contiguous pre-M1 domain (known as S1) and the loop between M3 and M4 (known as S2) parts of the GluK2 subunit [Contractor et al., 2011]. This includes the splice variants of the GluK2, GluK2a and GluK2b, which differ in their C-terminal domains and co-assemble as heteromers but do not show distinct functional properties [Coussen et al., 2005].

In another embodiment, the invention relates to a compound which is an antagonist of the heteromeric GluK2/GluK5 receptor or an inhibitor of the synaptic expression of heteromeric GluK2/GluK5 receptor for use in the treatment or the prevention of epilepsy.

In one embodiment, the epilepsy can be classified according the electroclinical syndromes following the Classification and Terminology of the International League Against Epilepsy (ILAE) [Berg et al., 2010]. These syndromes can be categorized by age at onset, distinctive constellations (surgical syndromes), and structural-metabolic causes: (A) age at onset: (i) neonatal period includes Benign familial neonatal epilepsy (BFNE), Early myoclonic encephalopathy (EME), Ohtahara syndrome. (ii) Infancy period includes Epilepsy of infancy with migrating focal seizures, West syndrome, Myoclonic epilepsy in infancy (MEI), Benign infantile epilepsy, Benign familial infantile epilepsy, Dravet syndrome, Myoclonic encephalopathy in nonprogressive disorders. (iii) Childhood period includes Febrile seizures plus (FS+), Panayiotopoulos syndrome, Epilepsy with myoclonic atonic (previously astatic) seizures, Benign epilepsy with centrotemporal spikes (BECTS), Autosomal-dominant nocturnal frontal lobe epilepsy (ADNFLE), Late onset childhood occipital epilepsy (Gastaut type), Epilepsy with myoclonic absences, Lennox-Gastaut syndrome, Epileptic encephalopathy with continuous spike-and-wave during sleep (CSWS), Landau-Kleffner syndrome (LKS), Childhood absence epilepsy (CAE). (iv) Adolescence—Adult period includes Juvenile absence epilepsy (JAE) Juvenile myoclonic epilepsy (JME), Epilepsy with generalized tonic—clonic seizures alone, Progressive myoclonus epilepsies (PME), Autosomal dominant epilepsy with auditory features (ADEAF), Other familial temporal lobe epilepsies. (v) Variable age onset includes Familial focal epilepsy with variable foci (childhood to adult), Reflex epilepsies. (B) Distinctive constellations (surgical syndromes) include Mesial Temporal Lobe Epilepsy (MTLE), Rasmussen syndrome, Gelastic seizures with hypothalamic hamartoma, Hemiconvulsion-hemiplegia-epilepsy. (C) Epilepsies attributed to and organized by structural-metabolic causes include Malformations of cortical development (hemimegalencephaly, heterotopias, etc.), Neurocutaneous syndromes (tuberous sclerosis complex, Sturge-Weber, etc.), Tumor, Infection, Trauma, Angioma, Perinatal insults, Stroke, Etc.

In another embodiment, the epilepsy may be a benign Rolandic epilepsy, a frontal lobe epilepsy, an infantile spasms, a juvenile myoclonic epilepsy, a juvenile absence epilepsy, a childhood absence epilepsy (pyknolepsy), a hot water epilepsy, a Lennox-Gastaut syndrome, a Landau-Kleffner syndrome, a Dravet syndrome, a progressive myoclonus epilepsies, a reflex epilepsy, a Rasmussen's syndrome, a temporal lobe epilepsy, a limbic epilepsy, a status epilepticus, an abdominal epilepsy, a massive bilateral myoclonus, a catamenial epilepsy, a Jacksonian seizure disorder, a Lafora disease or photosensitive epilepsy.

In a particular embodiment, the epilepsy is a temporal lobe epilepsy.

In one embodiment, the epilepsy is a chronic epilepsy.

In another embodiment, the epilepsy can be a refractory epilepsy.

As used herein, the term "refractory epilepsy" denotes an epilepsy which is refractory to current pharmaceutical treatment that is to say that current pharmaceutical treatment don't allow a treatment of patients (see for example Dario J. Englot et al., 2013).

In a particular embodiment, the refractory epilepsy is a chronic refractory epilepsy.

As used herein the term "Temporal Lobe Epilepsy" or "TLE" denotes a chronic neurological condition characterized by chronic and recurrent seizures (epilepsy) which originate in the temporal lobe of the brain. This disease is different from acute seizures in naïve brain tissue since in TLE morpho-functional re-organisation of neuronal network and sprouting of hippocampal mossy fibers appears whereas in acute seizures in naïve tissue such re-organisation is not present.

Thus, the invention also relates to a compound which is an antagonist of the GluK2/GluK5 receptor or an inhibitor of the GluK2/GluK5 receptors expression for use in the treatment or the prevention of epilepsy with -functional re-organisation of neuronal network and sprouting of hippocampal mossy fibers.

In one embodiment, the compound according to the invention is a GluK2/GluK5 receptor antagonist.

In one embodiment, said GluK2/GluK5 receptor antagonist may be a low molecular weight antagonist, e. g. a small organic molecule (natural or not).

The term "small organic molecule" refers to a molecule (natural or not) of a size comparable to those organic molecules generally used in pharmaceuticals. The term excludes biological macromolecules (e. g., proteins, nucleic acids, etc.). Preferred small organic molecules range in size up to about 10000 Da, more preferably up to 5000 Da, more preferably up to 2000 Da and most preferably up to about 1000 Da.

In a particular embodiment, the compound according to the invention is selected from the group consisting of UBP310, UBP302 and UBP316 and NBQX.

In a particular embodiment, the compound according to the invention is UBP310 an antagonist of the heteromeric kainate GluK2/GluK5 receptor [Pinheiro et al., 2013].

In another particular embodiment, the compound according to the invention is (2S,4R)-4-Methylglutamate (SYM2081), a compound that is a potent broad-spectrum agonist of kainate receptors; it binds to homomeric and heteromeric kainate receptors including homomeric GluK1, and GluK2 receptors and heteromeric GluK1/GluK2, GluK1/GluK5 and GluK2/GluK5 receptors [Jane et al., 2009]. This compound is currently used to selectively block kainate receptor signalling via desensitization of the receptors in control and epileptic conditions [Jane et al., 2009] [Li et al., 1999; Cossart et al., 2002; Epsztein et al., 2005; Epsztein et al., 2010; Joseph et al., 2011].

In another embodiment, the compound of the invention is a protein or a peptide.

In a particular embodiment, the protein or the peptide binds to the GluK2/GluK5 receptor cytosolic or membrane domain and prevents the recruitment or stabilisation of synaptic GluK2/GluK5 receptors. Thus, the protein or the peptide may be used in the treatment or the prevention of epilepsy.

In another embodiment, GluK2/GluK5 receptor antagonist of the invention may be an anti-GluK2/GluK5 antibody which neutralizes GluK2/GluK5 or an anti-GluK2/GluK5 fragment thereof which neutralizes GluK2/GluK5 [see for example Xie J H et Al., 2003].

In a particular embodiment, the antagonist of the invention may be an anti-GluK2/GluK5 subunit antibody or an anti-GluK2/GluK5 subunit fragment thereof.

Antibodies directed against GluK2/GluK5 receptor, GluK2 subunit or GluK5 subunit can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against GluK2/GluK5 receptor, GluK2 subunit or GluK5 subunit can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see e.g., U.S. Pat. No. 4,946,778) can be adapted to produce anti-GluK2/GluK5 receptor, anti-GluK2 subunit or anti-GluK5 subunit single chain antibodies. GluK2/GluK5 receptor, GluK2 subunit or GluK5 subunit antagonists useful in practicing the present invention also include anti-GluK2/GluK5 receptor, anti-GluK2 subunit or anti-GluK5 subunit antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to GluK2/GluK5 receptor, GluK2 subunit or GluK5 subunit.

Humanized anti-GluK2/GluK5 receptor, anti-GluK2 subunit or anti-GluK5 subunit antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then, for this invention, neutralizing antibodies of GluK2/GluK5 receptor, GluK2 subunit or GluK5 subunit are selected.

In still another embodiment, GluK2/GluK5 receptor, GluK2 subunit or GluK5 subunit antagonists may be selected from aptamers. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Then, for this invention, neutralizing aptamers of GluK2/GluK5 receptor, GluK2 subunit or GluK5 subunit are selected.

In another embodiment, the compound according to the invention is an inhibitor of the GluK2/GluK5 receptor expression.

In another embodiment, the compound according to the invention is an inhibitor of the synaptic expression of GluK2/GluK5 receptors.

As used herein, the term "inhibitor of the GluK2/GluK5 receptor expression" denotes a compound which inhibits the expression of the GluK2 subunit or the GluK5 subunit or both at synapses.

According to the invention an "inhibitor of the GluK2/GluK5 receptor expression" should lead to the partial or complete loss of synaptic GluK2/GluK5 receptors.

In a particular embodiment, the inhibitor of the invention is an inhibitor of the GluK2 subunit expression or an inhibitor of the GluK5 subunit expression for use in the treatment or the prevention of epilepsy.

Small inhibitory RNAs (siRNAs) can also function as inhibitors of GluK2/GluK5 receptor gene expression for use in the present invention. GluK2/GluK5 receptor gene expression can be reduced by contacting a subject or cell with a small double stranded RNA (dsRNA), or a vector or construct causing the production of a small double stranded RNA, such that GluK2/GluK5 receptor gene expression is specifically inhibited (i.e. RNA interference or RNAi). Methods for selecting an appropriate dsRNA or dsRNA-encoding vector are well known in the art for genes whose sequence is known (e.g. see for example Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of GluK2/GluK5 receptor gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of GluK2/GluK5 receptor mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of GluK2/GluK5 receptor gene expression can be prepared by known methods. These include techniques for chemical synthesis such as, e.g., by solid phase phosphoramidite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing GluK2/GluK5 receptor. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter. The promoter may be specific for Muller glial cells, microglia cells, endothelial cells, pericyte cells and astrocytes For example, a specific expression in Muller glial cells may be obtained through the promoter of the glutamine synthetase gene is suitable. The promoter can also be, e.g., a viral promoter, such as CMV promoter or any synthetic promoters.

In order to test the functionality of putative GluK2/GluK5 receptor antagonist on epilepsy, in vitro and in vivo tests will be performed. For in vitro tests, organotypic cortical and hippocampal slice cultures will be used since this in vitro model is highly suitable for studying spontaneous epileptiform activity [Albus et al., 2013; Dyhrfield-Johnsen et al., 2010; Zimmer and Gahwiler, 1984]. In vitro tests as explained in Barberis et al, 2008, or in Pinheiro et al, 2013 may also be used to test the effect of the putative antagonist on the function of recombinant GluK2/GluK5. For in vivo tests, experiments can be performed using an animal model of Temporal Lobe Epilepsy (for example the pilocarpine-status epilepticus model in rats or mice) [Loscher, 2002]. The test on putative GluK2/GluK5 receptor antagonist will be conducted during the chronic phase of Temporal Lobe Epilepsy i.e. several months after the inaugurating status epilepticus. Comparative test of GluK2/GluK5 receptor antagonist on the cardinal interictal and ictal discharges will be done using continuous cortical or intrahippocampal telemetric electroencephalographic (EEG) recordings (24 h per day).

Another object of the invention relates to a method for treating or preventing epilepsy comprising administering to a subject in need thereof a therapeutically effective amount of an antagonist of the GluK2/GluK5 receptor or an inhibitor of the GluK2/GluK5 receptor expression as described above.

In one aspect, the invention relates to a method for treating epilepsy comprising administering to a subject in need thereof a therapeutically effective amount of a GluK2/GluK5 antagonist as above described.

Compounds of the invention may be administered in the form of a pharmaceutical composition, as defined below.

Thus, another object of the invention relates to a pharmaceutical composition comprising an effective dose of an antagonist of the GluK2/GluK5 receptor or an inhibitor of the GluK2/GluK5 receptor expression for use in the treatment or prevention of epilepsy.

In one embodiment, the pharmaceutical composition according to the invention contains additionally a pharmaceutically acceptable carrier.

Particularly, said compound which is antagonist of the GluK2/GluK5 receptor or an inhibitor of the GluK2/GluK5 receptor expression.

In one embodiment, the composition as described below is used for treating or preventing epilepsy.

By a "therapeutically effective amount" is meant a sufficient amount of compound to treat and/or to prevent epilepsy.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Any therapeutic agent of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, parenteral, intravenous, intramuscular, intraperitoneal or subcutaneous administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

In addition, other pharmaceutically acceptable forms include, e.g. tablets or other solids for oral administration; time release capsules; and any other form currently can be used.

In one embodiment, the compound or the composition according to the invention may be delivered directly into the brain to directly reach neurons and/or astrocytes.

Methods of delivery of the compound or the composition of the invention to neurons and/or astrocytes includes generally any method suitable for delivery the compound or the composition of the invention to the neurons and/or astrocytes such that at least a portion of cells of a selected synaptically connected cell population is transduced. The compound or the composition of the invention may be delivered to any cells of the central nervous system, or both. Generally, the compound or the composition of the invention is delivered to the cells of the central nervous system, including for example dentate granule cells, cells of the spinal cord, brainstem (medulla, pons, and midbrain), cerebellum, diencephalon (thalamus, hypothalamus), telencephalon (hippocampus, corpus striatum, cerebral cortex, or, within the cortex, the occipital, temporal, parietal or frontal lobes), or combinations thereof, or preferably any suitable subpopulation thereof. Further preferred sites for delivery include the ruber nucleus, corpus amygdaloideum, entorhinal cortex and neurons in ventralis lateralis, or to the anterior nuclei of the thalamus.

To deliver the compound or the composition of the invention specifically to a particular region and to a particular population of cells of the CNS, the compound or the composition of the invention may be administered by stereotaxic microinjection. For example, patients have the stereotactic frame base fixed in place (screwed into the skull). The brain with stereotactic frame base (MRI compatible with fiducial markings) is imaged using high resolution MRI. The MRI images are then transferred to a computer which runs stereotactic software. A series of coronal, sagittal and axial images are used to determine the target (site of compound or composition injection) and trajectory. The software directly translates the trajectory into 3 dimensional coordinates appropriate for the stereotactic frame. Burr holes are drilled above the entry site and the stereotactic apparatus positioned with the needle implanted at the given depth. The compound or the composition of the invention is then injected at the target sites.

Additional routes of administration may also comprise local application of the compound or the composition of the invention under direct visualization, e. g., superficial cortical application, or other nonstereotactic application. The compound or the composition of the invention may be delivered intrathecally, in the ventricules or by intravenous injection.

The target cells of the compound or the composition of the invention of the present invention are cells of the central nervous systems of a subject afflicted with epilepsy's disease. Preferably the subject is a human being, generally an adult.

However the invention encompasses delivering the compound or the composition of the invention to biological models of the disease. In that case, the biological model may be any mammal at any stage of development at the time of delivery, e. g., embryonic, fetal, infantile, juvenile or adult, preferably it is an adult. Furthermore, the target CNS cells may be essentially from any source, especially nonhuman primates and mammals of the orders Rodenta (mice, rats, rabbit, hamsters), Carnivora (cats, dogs), and Arteriodactyla (cows, pigs, sheep, goats, horses) as well as any other non-human system (e. g. zebrafish model system).

Preferably, the method of the invention comprises intracerebral administration through stereotaxic injections. However, other known delivery methods may also be adapted in accordance with the invention. For example, for a more widespread distribution of the compound or the composition of the invention across the CNS, it may be injected into the cerebrospinal fluid, e. g., by lumbar puncture. To direct the compound or the composition of the invention to the peripheral nervous system, it may be injected into the spinal cord or into the peripheral ganglia, or the flesh (subcutaneously or intramuscularly) of the body part of interest. In certain situations the compound or the composition of the invention can be administered via an intravascular approach. For example, the compound or the composition of the invention can be administered intra-arterially (carotid) in situations where the blood-brain barrier is disturbed or not disturbed. Moreover, for more global delivery, the compound or the composition of the invention can be administered during the "opening" of the blood-brain barrier achieved by infusion of hypertonic solutions including mannitol.

Alternatively, the compound of the invention may be further identified by screening methods as hereinafter described.

Thus, another object of the invention relates to a method for screening a compound which is an antagonist of the GluK2/GluK5 receptor or an inhibitor of the GluK2/GluK5 receptor expression.

In particular, the invention provides a method for screening a compound which is an antagonist of the GluK2/GluK5 receptor or an inhibitor of the GluK2/GluK5 receptor expression for use in the treatment of epilepsy.

For example, the screening method may measure the binding of a candidate compound to the GluK2/GluK5 receptor, or to cells or membranes bearing the GluK2/GluK5 receptor or a fusion protein thereof by means of a label directly or indirectly associated with the candidate compound. Alternatively, a screening method may involve measuring or, qualitatively or quantitatively, detecting the competition of binding of a candidate compound to the receptor with a labelled competitor (e.g., antagonist).

In a particular embodiment, the screening method of the invention comprises the step consisting of:

a) providing a plurality of cells expressing the GluK2/GluK5 receptor:

b) incubating said cells with a candidate compound;

c) determining whether said candidate compound binds to the GluK2/GluK5 receptor; and d) selecting the candidate compound that antagonises the GluK2/GluK5 receptor or that prevents the activation of the pathway receptor or that prevents the formation of the heteromeric complex GluK2/GluK5.

In general, such screening methods involve providing appropriate cells which express the GluK2/GluK5 receptor, its orthologs and derivatives thereof on their surface. In particular, nucleic acids encoding the GluK2 and GluK5 receptor subunits may be employed to co-transfect cells to thereby express the GluK2/GluK5 receptor. Such a transfection may be achieved by methods well known in the art.

In a particular embodiment, cells may be neuronal cells.

According to a one embodiment of the invention, the candidate compound may be selected from a library of compounds previously synthesised, or a library of compounds for which the structure is determined in a database, or from a library of compounds that have been synthesised de novo or natural compounds.

The candidate compound may be selected from the group of (a) proteins or peptides, (b) nucleic acids and (c) organic or chemical compounds (natural or not). Illustratively, libraries of pre-selected candidate nucleic acids may be obtained by performing the SELEX method as described in documents U.S. Pat. No. 5,475,096 and U.S. Pat. No. 5,270,163. Further illustratively, the candidate compound may be selected from the group of antibodies directed against the GluK2/GluK5 receptor.

The invention will be further illustrated by the following figures and examples. However, these examples and figures should not be interpreted in any way as limiting the scope of the present invention.

FIGURES

FIG. 1: Reduced epileptiform activity in dentate gyrus of organotypic slices from GluK2−/− mice. (A) Frequency of epileptiform activity recorded in WT and GluK2−/− slices. *$P<0.001$ by Mann-Whitney U test (n=32 and n=25 slices, respectively). (B) Power spectrum analysis (left) of filtered PDs and maximum power in each group (right). $P>0.05$ by Mann-Whitney U test (n=32 and n=25 slices). (C) Power spectrum analysis (left) of filtered MBs and maximum power in each group (right). $P<0.01$ by Mann-Whitney U test (n=32 and n=25 slices per group). In this and following figures: error bars=sem.

FIG. 2: Kainate receptor antagonists decrease epileptiform activity in dentate gyrus of organotypic slices from WT mice. (A) Frequency of epileptiform activity recorded in the presence and absence of 5 μM UBP310 (*$P<0.05$, n=32 and n=11) or 10 μM SYM2081 (*$P<0.05$, n=32 and n=10); Mann-Whitney U test. (B) Power spectrum analysis of filtered PDs (left) and the maximum value of the power (right). $P>0.05$ by Mann-Whitney U test (n=10-32 slices per group). (C) Power spectrum analysis of filtered MBs (left) and maximum power in each group (right). ***$P<0.001$, *$P<0.05$ by Mann-Whitney U test (n=10-32 slices per group).

FIG. 3: EPSCs with slow kinetics are important determinants of epileptiform activity. (A) Frequency of epileptiform activity. ***$P<0.001$ by Mann-Whitney U test (n=32 in WT, n=25 in GluK2−/− and n=10 in GluK2−/−+CTZ). (B) Power spectrum analysis of filtered MBs. *$P<0.05$ by Mann-Whitney U test.

FIG. 4: Evoked bursts are reduced in dentate gyrus of GluK2−/− mice and by UBP310 in WT mice. (A) $EPSC_{KA}$ amplitude before and after UBP310 in WT slices (A, $P<0.01$ by Wilcoxon test, n=9). (B) $EPSC_{AMPA}$ amplitude before and after GYKI53655 in GluK2−/− slices (B,*$P<0.001$ by Wilcoxon test, n=11). (C) Mean coastline burst index in WT slices before and after UBP310 or in GluK2−/− slices. $P<0.01$, *$P<0.001$ by Mann-Whitney U test (n=5-11 slices per group).

FIG. 5: The number of Interictal Spikes (ISs) and Ictal Discharges are decreased in in-vivo in GluK2−/− mice and by UBP310 in WT mice. (A) Number of ISs/min in WT (n=14) and GluK2−/− mice (n=8); *$P=0.012$ by unpaired t test (left). Number of ISs/min before (n=6) and after 60 mg/kg UBP310 (n=6); *$P=0.0313$ by Wilcoxon test (right). (B) Pie chart showing the fraction of ictal discharges recorded in WT (n=5) and GluK2−/− (n=5) mice (193 and 55 ictal discharges in WT and GluK2−/− mice, respectively)(left). Number of ictal discharges in WT (n=5) and GluK2−/− mice (n=5) per day; *$P=0.031$ by Mann-Whitney U test (middle). Number of ictal discharges before and during treatment with 60 mg/kg UBP310 (n=5); **$P=0.005$ by paired t test (right).

EXAMPLE

Material & Methods

Mouse Model of Temporal Lobe Epilepsy.

All experiments were approved by the Institut National de la Santé et de la Recherche Médicale animal care and use committee of May 29, 2001 (2001-464) and the European community council directive of Nov. 24, 1986 (86/609/EEC). Mice (FVB/N background) had access to food and water ad libitum and were housed under a 12 h light/dark cycle at 22-24° C. Male GluK2−/− and WT mice (P60-80) were given scopolamine (1 mg/kg) subcutaneously (s.c.) 15 minutes prior to s.c. administration of pilocarpine (200-600 mg/kg). A ramp protocol was used whereby animals were given an initial dose of 200 mg/kg followed by half-doses every 30 minutes until seizures appeared. Both WT and GluK2−/− mice typically experienced at least two seizures prior to entering status epilepticus (SE). Diazepam (10 mg/kg) was administered 45 minutes after onset of SE.

Slice Culture.

Hippocampal/entorhinal cortex slices (350 μm) were prepared from pre-genotyped GluK2−/− and WT mice (P9-10, FVB/N background) using a McIlwain tissue chopper. Slices were placed on mesh inserts (Millipore # PICMORG50) inside culture dishes containing 1 ml of the following medium: MEM 50%, HS 25%, HBSS 25%, HEPES 15 mM glucose 6.5 mg/ml and insulin 0.1 mg/ml. Culture medium was changed every 2-3 days and slices maintained in an incubator at 37° C./5% CO2. Pilocarpine (0.5 μM) was added to the medium at 5 D.I.V and removed at 7 D.I.V; slices were utilized for experiments from 9 D.I.V.

Acute Slice Preparation.

Hippocampal slices were prepared from pilocarpine-treated and control GluK2−/− and WT mice, at 5-9 months of age. Animals were deeply anesthetized with xylazine 13 mg/kg/ketamine 66 mg/kg and transcardially perfused with a modified artificial cerebrospinal fluid (mACSF) containing the following (in mM): 132 choline, 2.5 KCl, 1.25 NaH2PO4, 25 NaHCO3, 7 MgCl2, 0.5 CaCl2, and 8 D-glucose prior to decapitation. The brain was then removed rapidly, the hippocampi were dissected, and transverse 350 μM thick slices were cut using a Leica VT1200S vibratome in ice-cold oxygenated (95% O2 and 5% CO2) mACSF. Slices were transferred to rest at ~30° C. for 30 min and then room temperature for a further 30 min, in oxygenated solution containing 50% mACSF and 50% normal ACSF containing the following (in mM): 126 NaCl, 3.5 KCl, 1.2 NaH2PO4, 26 NaHCO3, 1.3 MgCl2, 2.0 CaCl2, and 10 D-glucose, pH 7.4.

Electrophysiological Recordings and Analysis.

Cultured or acute slices were individually transferred to a recording chamber maintained at 30-32° C. and continuously perfused (2 ml/min) with oxygenated normal or adapted ACSF containing 5 μM gabazine. Local field potentials were made in the granule cell layer of the DG with glass electrodes (2-3 MΩ; filled with normal ACSF) using a DAM-80 amplifier (low filter, 1 Hz; highpass filter, 3 KHz;

World Precision Instruments, Sarasota, Fla.). For evoked synaptic transmission, electrical stimulation was performed with a bipolar NiCh electrode (#762000, AM systems). Whole-cell voltage-clamp recordings of DGCs were made using tight-seal electrodes (5-8 MΩ) filled with an internal solution containing the following (in mM): 135 gluconic acid, 135 CsOH, 10 MgCl2, 0.1 CaCl2, 1 EGTA, 10 HEPES, 2 MgATP, 0.4 NaGTP, and 0.5% biocytin, pH 7.25. We used a Multiclamp 700B amplifier (Molecular Devices): data were filtered at 2 kHz, digitized (20 kHz) with a Digidata 1440A (Molecular Devices) to a PC, and acquired using Clampex 10.1 software (PClamp, Molecular Devices). Signals were analyzed off-line using Clampfit 9.2 (PClamp) and MiniAnalysis 6.0.1 (Synaptosoft, Decatur, Ga.). In organotypic slices, spontaneous EPSCs were recorded at the reversal potential for GABAergic currents (Vh=−70 mV). To characterize the nature and kinetic properties of fast and slow events, miniature EPSCs (mEPSCs) evoked in Sr2+ conditions (external Ca2+ was substituted with 1.2 mM Sr2+) were recorded in DGCs from GluK2−/− and WT slices. Electrical stimulation was made in the molecular layer in the continued presence of 5 μM gabazine and 40 μM D-APV; asynchronous mEPSCs were measured during the 300 ms period after the stimulus artifact. WT cultured slices displayed slowly decaying spontaneous and mEPSCs mediated by KARs (Epsztein et al., 2005). KAR-mediated mEPSCs were insensitive to the AMPAR antagonist GYKI53655 and abolished in the presence of the broad spectrum KAR antagonist SYM2081 (10 μM) (Epsztein et al., 2005; Epsztein et al., 2010; Artinian et al., 2011) or 5 μM UBP310, a potent antagonist of KAR at mossy fiber-CA3 synapses (Pinheiro et al., 2013). These events were absent in GluK2−/− slices (data not shown); the remaining fast EPSCs were fully blocked by AMPAR antagonist GYKI53655 (30 μM) in GluK2−/− slices (data not shown). In cultured slices, visual representation of time-frequency analysis of local field potentials was performed using Autosignal software (Seasolve 1.7). In brief, field activity was highpass-filtered (>100 Hz) and time-frequency analysis performed using a continuous wavelet (Morlet) that reported integrated power (time-integral-squared amplitude, TISA) across time. Filtered traces were also analyzed by Fourier analysis (Hamming) using Clampfit 9.2. In acute hippocampal slices, intensity of antidromically-evoked bursts was quantified using coastline index (Epsztein et al., 2005).

Electrophysiological Analysis In Vivo.

Naïve wildtype (WT) and pilocarpine-treated WT or GluK2−/− mice (5-6 months old) were anaesthetized with xylazine 13 mg/kg/ketamine 66 mg/kg and placed in a stereotaxic frame (supplemental dosing was administered as required). Body temperature was maintained using a heating pad. The scalp was removed and a small bone window was drilled above the hippocampus (2.1 mm posterior to bregma and 1.4 mm lateral to midline over the right hemisphere). For local field potentials recordings performed in anaesthetized mice, a glass electrode (~5 mΩ) filled with Ringer solution (135 mM NaCl, 5.4 mM KCl, 1 mM MgCl2, 1.8 mM CaCl2, 5 mM HEPES) was inserted into the DG (depth, 1650 μm). Recordings were performed using a DAM-80 amplifier (low filter, 1 Hz; high filter, 3 KHz; World Precision Instruments, Sarasota, Fla.). UBP310 or vehicle (saline/ 10% DMSO) was subsequently injected intraperitoneally (i.p.). During recordings and subsequent analysis, the experimenter was blind to the genotype. For intrahippocampal electroencephalographic (EEG) recordings performed in freely-moving animal a stainless steel electrode (Plastic one, Roanoke, Va.) was inserted into the DG under anesthesia (see above). After a 4 day recovery, EEG (amplified (1000×), filtered at 0.16-97 Hz pass, acquired at 500 Hz) was monitored using a telemetric system (Data Sciences International, St. Paul, Minn.) for 4 days, 24 h per day. Intrahippocampal EEG traces represented the difference in potential between the electrode inserted into the DG and an electrode positioned above the cerebellum; food and water were given ad libitum. UBP310 or vehicle (saline/10% DMSO) was injected intraperitoneally twice a day.

Mossy fiber staining—synaptoporin: Cultured organotypic slices were fixed and incubated with primary antibody against synaptoporin (SPO: Synaptic systems, 1:300) in PBS containing bovine serum albumin (1%) and normal goat serum (5%) for 2 days at 4° C. under agitation. Slices were then washed, placed in secondary antibody Alexa555 (Invitrogen 1:500) for 2 hours and counterstained with Neurotracer fluorenscent Nissl (invitrogen). SPO immunofluorescence was visualized using a Zeiss confocal microscope and quantitative analysis of optical density (OD) of fluorescence was assessed in the molecular and granule cell layers using a custom-made ImageJ programme (T. Tressard, INMED, INSERM U901). Only slices that displayed clear fluorescence in the stratum lucidum were used for analysis. Measurements were also made in the subiculum, a region with consistently low levels of staining, to ascertain background fluorescence and subsequently subtracted to account for variability in SPO staining in individual slices. All analysis was performed blind using slices from GluK2−/− and WT mice; the mean OD of fluorescence in the granule and molecular layers was calculated for each group.

Biocytin and Prox1 Revelation of DGCs.

As organotypic slice cultures display some dispersion of DGCs, cells that were recorded in whole-cell configuration were filled with biocytin, and subsequently labelled with Prox1, a granule cell marker; prox1-negative cells were excluded from electrophysiological analysis. Slices were fixed then permeabilized (0.5% Triton) in blocking solution containing 5% normal goat serum (NGS) in 0.5% Triton for 1 hour at room temperature. Slices were then incubated in the polyclonal rabbit anti-Pox1 antibody (Millipore) at 1:2000 in 5% NGS in 0.5% Triton overnight at 4° C. Slices were incubated for 2 hours in secondary antibody (Alexa Fluor 488, invitrogen) then coverslipped in fluoromount. For biocytin revelation, slices were fixed, washed and then incubated overnight (4° C.) with streptavidin conjugated to Cy3 (Jackson) diluted 1:500 in a solution containing 2% NGS and 0.3% Triton.

Statistics Analyses.

All values are given as means+SEM. Statistical analyses were performed using Graphpad Prism (GraphPad software, version 5.01). For comparison between groups with normal distribution, the two-sample unpaired or paired Student's t test was used for two groups. When data were not normally distributed, the Mann-Whitney rank-sum test (for unpaired data) or the two-sample Kolmogorov-Smirnov rank-sum test (for paired data) was used. Percentage values indicated in the text are calculated using paired data except when WT and GluK2−/− groups are compared.

Pharmacological Agents.

Gabazine (SR-95531); D-APV; GYKI53655; SYM2081 and DCGIV were purchased from Tocris Bioscience. Cyclothiazide and UBP310 were purchased from ABCAM. Scopolamine methyl nitrate and pilocarpine hydrochloride were purchased from sigma, diazepam from Roche.

Results

Removal of KARs Reduces Epileptiform Activity in the DG in Organotypic Slices

In a first attempt to elucidate whether KARs play any role in spontaneous epileptiform discharges in the DG, we used organotypic hippocampal slice cultures treated with pilocarpine. This in vitro model is highly suitable for studying mossy fiber sprouting and spontaneous epileptiform activity (Zimmer and Gahwiler, 1984; McBain et al., 1989; Gutierrez and Heinemann, 1999; Thomas et al., 2005; Dyhrfield-Johnsen et al., 2010; Grabs et al., 1994; Albus et al., 2013). We observed a similar sprouting of mossy fibers in WT (n=32) and GluK2-/- (n=27) slices following incubation with pilocarpine as revealed by synaptoporin (SPO) staining (Grabs et al., 1994) (see methods) (OD: 26.1±2.9 in WT and 25.0±3.0 in GluK2-/-, P>0.05, data not shown). Accordingly, the frequency of ongoing excitatory postsynaptic currents (EPSCs) was similar in DGCs from WT and GluK2-/- slices (P>0.05, not shown). In chronically epileptic rodents but not in naïve animals, slow KAR-mediated synaptic events occur in DGCs due to recurrent mossy fibers (Epsztein et al., 2005; Epsztein et al., 2010; Artinian et al., 2011). We confirmed that organotypic slices from WT mice also displayed slowly decaying spontaneous and miniature EPSCs mediated by KARs (see methods; data not shown). These events were absent in GluK2-/- slices highlighting the importance of the GluK2 subunit in aberrant synaptic activity; the remaining fast EPSCs were mediated by AMPARs (data not shown). That KAR-EPSCs were generated at recurrent mossy fiber synapses was confirmed using the group II mGluR agonist DCGIV (Feng et al., 2003; Epsztein et al., 2005) (data not shown).

The role of KARs in spontaneous epileptiform activity was then tested using extracellular field recordings in cultured slices. Recordings were performed in 5 mM K+-containing ACSF and in the presence of 5 µM gabazine in order to enhance neuronal excitability and to reliably record stereotyped spontaneous interictal-like activity (Berdichevsky et al., 2012). In keeping with previous reports, the interical-like activity consisted of two distinct phases: first, the paroxysmal discharge (PD) followed by a late phase containing multiple recurrent bursts (MBs) (McBain et al., 1989; Gutierrez and Heinemann, 1999; Thomas et al., 2005; Dyhrfjeld-Johnsen et al., 2010) (data not shown). The frequency of interictal-like activity was markedly reduced in cultured slices from GluK2-/- mice, by 46% in comparison with WT (events/min: from 3.2±0.4 in WT to 1.7±0.3 in GluK2-/-) (FIG. 1A). The interictal-like activity nested pathological high frequency oscillations with a peak frequency range of 250-300 Hz (n=32) (data not shown) in agreement with previous observations (Bragin et al., 2004; Dyhrfjeld-Johnsen et al., 2010). We studied the power of the pathological high frequency activity within the two phases of interictal-like activity. Activity was visualized by high-pass filtering (data not shown) and by time-frequency representations (not shown). Power analysis revealed no alteration in the PD phase of the activity (FIG. 1B). Conversely, power during the late phase of MBs was markedly reduced by 77% in GluK2-/- mice (FIG. 1C).

The role of KARs in the interictal-like activity of cultured slices was further assessed pharmacologically using SYM2081, a broad spectrum KAR antagonist (Epsztein et al., 2005; Epsztein et al., 2010; Artinian et al., 2011) or UBP310, a potent antagonist of postsynaptic GluK2/GluK5 KAR at mossy fiber-CA3 synapses (Pinheiro et al., 2013). In slices from WT mice, the frequency of interictal-like activity was significantly reduced in the presence of KAR antagonists: by 47% in SYM2081 (events/min: 3.2±0.4 vs. 1.69±0.3 in SYM2081) and by 49% in UBP310 (1.47±0.4 in UBP310) (FIG. 2A). A similar reduction of interictal-like activity was observed in the presence of UBP310 in slices in which cuts were made to isolate the DG (data not shown) indicating that the activity originated from and propagated within the DG itself. No significant alteration of the PD phase was observed in the presence of either SYM2081 or UBP310 (FIG. 2B). In contrast, the late MB phase was significantly disrupted in the presence of KAR antagonists; the power of the bursts was reduced by 68% in SYM2081 and by 67% in UBP310 (FIG. 2C). In support of the importance of the GluK2 subunit, we observed that (i) there was no effect on interictal-like activity in the presence of UBP310 in GluK2-/- mice (P=0.563, n=7); (ii) the frequency of interictal-like activity was similar in slices from GluK1-/- and WT mice (P=0.936, n=6) in contrast to GluK2-/- mice. (iii) UBP310 was similarly effective to reduce the frequency of interictal-like activity in WT and in GluK1-/- mice (P=0.902, n=6).

One of the specific features of KAR-mediated EPSCs compared to those mediated by AMPARs is their slow kinetics (Castillo et al., 1997; Frerking et al., 1998; Bureau et al., 2000; Ben-Ari and Cossart, 2000; Epsztein et al., 2005; Zhang et al., 2009; Copits et al., 2011). Therefore, we hypothesized that this particular feature was likely to be an important determinant of interictal-like activity. To primarily test the kinetics hypothesis, we used cyclothiazide (CTZ) to slow the decay kinetics of AMPAR-mediated EPSCs, and hence to mimic the slow kinetics of KAR-mediated EPSCs in DG cells, in GluK2-/- mice which lack slow synaptic events (data not shown). Reduced interictal-like activity observed with extracellular field potential recordings in GluK2-/- slices could be recovered with bath application of CTZ (FIG. 3A/B). This shows that synaptic events with slow kinetics are important for the genesis of interictal-like activity.

Therefore, these experiments demonstrate that KARs containing the GluK2/GluK5 subunits play a central role in interictal-like activity in this in vitro model of TLE.

KAR involvement in Burst Activity is Driven by Recurrent Mossy Fibers in DG

Experiments performed in cultured slices, have provided strong evidence for a role of KARs in epileptiform discharges in the DG. We then asked whether this observation could be established in an animal model of TLE. To this end, experiments were performed in pilocarpine-treated WT or GluK2-/- mice several months after the inaugurating status epilepticus (see methods). Under these conditions, similar sprouting of mossy fibers was observed in both WT (n=33) and GluK2-/- (n=25) mice (OD: 15.9±1.1 in WT and 20.9±3.9 in GluK2-/-, P>0.05, data not shown) but not in naïve conditions (data not shown) as revealed by SPO staining (Grabs et al., 1994). This indicates that GluK2 does not play a role in the establishment of recurrent mossy fiber connections in the pilocarpine model of TLE in agreement with findings in cultured slices. Accordingly, recordings in acute hippocampal slices several months after the inaugurating status epilepticus, revealed a similar frequency of ongoing EPSCs in DGCs from WT and GluK2-/- slices (P>0.05, not shown). By stimulating in the inner third of the molecular layer and thereby targeting the sprouted mossy fibers, KAR-mediated EPSCs could be recorded in DGCs from WT, while only AMPA-mediated EPSCs were recorded in DGCs from GluK2-/- slices (FIG. 4 A/B). KAR-mediated EPSCs were generated at mossy fiber synapses since they were strongly inhibited by DCGIV (1 µM, by 84%, data not shown). Next we tested the role of KARs in epileptiform activity driven by recurrent mossy fibers. Bursts were evoked by antidromic stimulation of the mossy fiber pathway in the CA3b area while recording local field potentials in the DGC layer (data not shown). In WT mice, blockade of KARs by bath application of UBP310 strongly reduced bursts (by 55%) (see methods) (FIG. 4 C). Accordingly, bursts were significantly lower in GluK2−/− mice compared to WT (reduced by 63%) (FIG. 4 C).

Thus, KARs containing the GluK2/GluK5 subunits play a central role in burst activity driven by recurrent mossy fibers in the DG.

Frequency of Interictal Spikes and Ictal Discharges In Vivo are Reduced in the Absence of KARs In TLE, interictal spikes (ISs) represent one of the best documented biomarkers of epilepsy in patient and animal models (Staley et al., 2005). We attempted to extend our in vitro findings to the whole-animal model and asked whether KARs are involved in this type of chronic pathological activity in TLE in the DG. Local field potential recordings were performed in vivo on anesthetized naïve and pilocarpine-treated mice. As previously reported (Turski et al., 1984), recordings from WT epileptic mice displayed numerous ISs (137.2+27.9 ISs/min) several months after inaugurating status epilepticus, but this type of activity was never observed in naïve animals (n=5). Remarkably, in GluK2−/− mice, the number of ISs was strongly reduced by 84% in comparison with WT (21.6+7.5 ISs/min, FIG. 5A). This reduction was not associated with a significant change in IS amplitude (data not shown). Then, we tested the effects of a KAR antagonist on ISs. Intraperitoneal injection of 60 mg/kg of UBP310 significantly reduced the number of ISs (by 64%) (FIG. 5A) with no change in amplitude (data not shown). When the injected dose of UBP310 was reduced by 10 times there was no significant effect of the drug on IS number (P=0.548). No significant effect was observed with injection of vehicle (data not shown). In addition, in support of the importance of the GluK2 subunit, there was no effect on the number of ISs by injecting UBP310 (60 mg/kg) in GluK2−/− mice (P=0.497, data not shown).

In temporal lobe epilepsy, the cardinal pathophysiological electroencephalographic (EEG) activity is recurrent ictal discharges originating from limbic structures including the hippocampus and leading to profound disabling clinical manifestations. These ictal events are due to abnormal and long lasting (tens of seconds) hypersynchronous neuronal activity. To definitively test the role of KARs on ictal discharges, intrahippocampal EEG recordings were performed in the DG of freely-moving WT and GluK2−/− pilocarpine-treated mice several months after inaugurating status epilepticus. EEG was continuously monitored for several days using a telemetric system (ee methods). WT mice displayed numerous ictal discharges (9.6+2.3 per day) lasting 36.9+1.8 s (n=5) and including tonic and clonic phases. These ictal events corresponded to the well described generalized tonic-clonic seizures with motor convulsions and loss of postural control (not shown). When comparing WT and GluK2−/− mice we observed a strong reduction of the number of ictal events (by 71%, FIG. 5B) without a significant change in their duration (P>0.05). The reduction of ictal discharges observed in GluK2$^{-/-}$ mice was corroborated by the use of UBP310. Indeed, intraperitoneal injections for 3 days of UBP310 (60 mg/kg, see methods) significantly reduced the number of ictal events (by 41%) (FIG. 5B) without a significant change in their duration (P=0.286). No significant effect was observed with injection of vehicle (data not shown).

Therefore, KARs are crucially involved in the generation of both ISs and ictal discharges in vivo in epileptic mice. Taken together, these experiments demonstrate that aberrant KARs containing the GluK2/GluK5 subunits play a major role in epileptic activity in the chronic phase of TLE.

CONCLUSION

The inventors show for the time that heteromeric GluK2/GluK5 receptor which is a receptor with different pharmacological properties than homomeric GluK2 receptors or GluK1 receptor plays an important role in epilepsy and especially in chronic epilepsy.

More important, they show that in a chronic model of epilepsy, that is to say, a status epilepticus model (induced by a convulsive agent like pilocarpine injection) and in which the disease has had time to settle (with morpho-functional re-organisation of neuronal network and sprouting of hippocampal mossy fibers), the use of an antagonist of the GluK2/GluK5 receptor could represent an important alternative to treat chronic epilepsy (TLE) in patient. This is the first time that results with KAR antagonists are obtained for chronic epilepsy models; the state of the art only shows effects of KAR agents on acute seizures (that is to say directly after an injection of a convulsive chemical agent without morpho-functional re-organisation of neuronal network and sprouting of hippocampal mossy fibers).

REFERENCES

Throughout this application, various references describe the state of the art to which this invention pertains. The disclosures of these references are hereby incorporated by reference into the present disclosure.

Albus K, Heinemann U, Kovacs R (2013) Network activity in hippocampal slice cultures revealed by long-term in vitro recordings. J Neurosci Methods 217:1-8.

Artinian J, Peret A, Marti G, Epsztein J, Crepel V (2011) Synaptic kainate receptors in interplay with INaP shift the sparse firing of dentate granule cells to a sustained rhythmic mode in temporal lobe epilepsy. J Neurosci 31:10811-10818.

Ben-Ari Y, Cossart R (2000) Kainate, a double agent that generates seizures: two decades of progress. Trends Neurosci 23:580-587.

Berdichevsky Y, Dzhala V, Mail M, Staley K J (2012) Interictal spikes, seizures and ictal cell death are not necessary for post-traumatic epileptogenesis in vitro. Neurobiol Dis 45:774-785.

Berg A T, Berkovic S F, Brodie M J, Buchhalter J, Cross J H, van Emde B W, Engel J, French J, Glauser T A, Mathern G W, Moshe S L, Nordli D, Plouin P, Scheffer I E (2010) Revised terminology and concepts for organization of seizures and epilepsies: report of the ILAE Commission on Classification and Terminology, 2005-2009. Epilepsia 51:676-685.

Bragin A, Wilson C L, Almajano J, Mody I, Engel J, Jr. (2004) High-frequency oscillations after status epilepticus: epileptogenesis and seizure genesis. Epilepsia 45:1017-1023.

Buckmaster P S, Zhang G F, Yamawaki R (2002) Axon sprouting in a model of temporal lobe epilepsy creates a predominantly excitatory feedback circuit. J Neurosci 22:6650-6658.

Bureau I, Dieudonne S, Coussen F, Mulle C (2000) Kainate receptor-mediated synaptic currents in cerebellar Golgi cells are not shaped by diffusion of glutamate. Proc Natl Acad Sci USA 97:6838-6843.

Castillo P E, Malenka R C, Nicoll R A (1997) Kainate receptors mediate a slow postsynaptic current in hippocampal CA3 neurons. Nature 388:182-186.

Contractor A, Mulle C, Swanson G T (2011) Kainate receptors coming of age: milestones of two decades of research. Trends Neurosci 34:154-163.

Copits B A, Robbins J S, Frausto S, Swanson G T (2011) Synaptic targeting and functional modulation of GluK1 kainate receptors by the auxiliary neuropilin and tolloid-like (NETO) proteins. J Neurosci 31:7334-7340.

Cossart R, Epsztein J, Tyzio R, Becq H, Hirsch J, Ben-Ari Y, Crepel V (2002) Quantal release of glutamate generates pure kainate and mixed AMPA/kainate EPSCs in hippocampal neurons. Neuron 35:147-159.

Coussen F, Perrais D, Jaskolski F, Sachidhanandam S, Normand E, Bockaert J, Marin P, Mulle C (2005) Co-assembly of two GluR6 kainate receptor splice variants within a functional protein complex. Neuron 47:555-566.

Dario J. Englot, M.D., Ph.D., John D. Rolston, M.D., Ph.D., Doris D. Wang, M.D., Ph.D., Peter P. Sun, M.D., Edw and F. Chang, M.D. Seizure outcomes after temporal lobectomy in pediatric patients. J Neurosurg Pediatrics 12:134-141, 2013.

and Kurtis I. Auguste, M.D.1,2

Dyhrfield-Johnsen J, Berdichevsky Y, Swiercz W, Sabolek H, Staley K J (2010) Interictal spikes precede ictal discharges in an organotypic hippocampal slice culture model of epileptogenesis. J Clin Neurophysiol 27:418-424.

Epsztein J, Represa A, Jorquera I, Ben-Ari Y, Crepel V (2005) Recurrent mossy fibers establish aberrant kainate receptor-operated synapses on granule cells from epileptic rats. J Neurosci 25:8229-8239.

Epsztein J, Sola E, Represa A, Ben-Ari Y, Crepel V (2010) A selective interplay between aberrant EPSPKA and INaP reduces spike timing precision in dentate granule cells of epileptic rats. Cereb Cortex 20:898-911.

Feng L, Molnar P, Nadler J V (2003) Short-term frequency-dependent plasticity at recurrent mossy fiber synapses of the epileptic brain. J Neurosci 23:5381-5390.

Franck J E, Pokorny J, Kunkel D D, Schwartzkroin P A (1995) Physiologic and morphologic characteristics of granule cell circuitry in human epileptic hippocampus. Epilepsia 36:543-558.

Frerking M, Malenka R C, Nicoll R A (1998) Synaptic activation of kainate receptors on hippocampal interneurons. Nat Neurosci 1:479-486.

Gabriel S, Njunting M, Pomper J K, Merschhemke M, Sanabria E R, Eilers A, Kivi A, Zeller M, Meencke H J, Cavalheiro E A, Heinemann U, Lehmann T N (2004) Stimulus and potassium-induced epileptiform activity in the human dentate gyms from patients with and without hippocampal sclerosis. J Neurosci 24:10416-10430.

Grabs D, Bergmann M, Schuster T, Fox P A, Brich M, Gratz M (1994) Differential expression of synaptophysin and synaptoporin during pre- and postnatal development of the rat hippocampal network. Eur J Neurosci 6:1765-1771.

Gutierrez R, Heinemann U (1999) Synaptic reorganization in explanted cultures of rat hippocampus. Brain Res 815:304-316.

Isokawa M, Levesque M F, Babb T L, Engel J, Jr. (1993) Single mossy fiber axonal systems of human dentate granule cells studied in hippocampal slices from patients with temporal lobe epilepsy. J Neurosci 13:1511-1522.

Jane D E, Lodge D, Collingridge G L (2009) Kainate receptors: pharmacology, function and therapeutic potential. Neuropharmacology 56:90-113.

Joseph D J, Williams D J, MacDermott A B (2011) Modulation of neurite outgrowth by activation of calcium-permeable kainate receptors expressed by rat nociceptive-like dorsal root ganglion neurons. Dev Neurobiol 71:818-835.

Li P, Wilding T J, Kim S J, Calejesan A A, Huettner J E, Zhuo M (1999) Kainate-receptor-mediated sensory synaptic transmission in mammalian spinal cord. Nature 397:161-164.

Loscher W (2002) Animal models of epilepsy for the development of antiepileptogenic and disease-modifying drugs. A comparison of the pharmacology of kindling and post-status epilepticus models of temporal lobe epilepsy. Epilepsy Res 50:105-123.

Lynch M, Sutula T (2000) Recurrent excitatory connectivity in the dentate gyms of kindled and kainic acid-treated rats. J Neurophysiol 83:693-704.

McBain C J, Boden P, Hill R G (1989) Rat hippocampal slices 'in vitro' display spontaneous epileptiform activity following long-term organotypic culture. J Neurosci Methods 27:35-49.

Mello L E, Cavalheiro E A, Tan A M, Kupfer W R, Pretorius J K, Babb T L, Finch D M (1993) Circuit mechanisms of seizures in the pilocarpine model of chronic epilepsy: cell loss and mossy fiber sprouting. Epilepsia 34:985-995.

Okazaki M M, Evenson D A, Nadler J V (1995) Hippocampal mossy fiber sprouting and synapse formation after status epilepticus in rats: visualization after retrograde transport of biocytin. J Comp Neurol 352:515-534.

Patrylo P R, Dudek F E (1998) Physiological unmasking of new glutamatergic pathways in the dentate gyrus of hippocampal slices from kainate-induced epileptic rats. J Neurophysiol 79:418-429.

Peret A, Christie L A, Ouedraogo D W, Gorlewicz A, Epsztein J, Mulle C, Crepel V. Contribution of Aberrant GluK2-Containing Kainate Receptors to Chronic Seizures in Temporal Lobe Epilepsy. Cell Rep. 2014 Jul. 24.

Pinheiro P. and Mulle Christophe. Kainate receptors. Cell Tisses Res, 2006.

Pinheiro P S, Lanore F, Veran J, Artinian J, Blanchet C, Crepel V, Perrais D, Mulle C (2013) Selective block of postsynaptic kainate receptors reveals their function at hippocampal mossy fiber synapses. Cereb Cortex 23:323-331.

Reiner A, Arant R J, Isacoff E Y (2012) Assembly stoichiometry of the GluK2/GluK5 kainate receptor complex. Cell Rep 1:234-240.

Represa A, Le Gall La S G, Ben-Ari Y (1989a) Hippocampal plasticity in the kindling model of epilepsy in rats. Neurosci Lett 99:345-350.

Represa A, Robain O, Tremblay E, Ben An Y (1989b) Hippocampal plasticity in childhood epilepsy. Neurosci Lett 99:351-355.

Scharfman H E, Sollas A L, Berger R E, Goodman J H (2003) Electrophysiological evidence of monosynaptic excitatory transmission between granule cells after seizure-induced mossy fiber sprouting. J Neurophysiol 90:2536-2547.

Staley K, Hellier J L, Dudek F E (2005) Do interictal spikes drive epileptogenesis? Neuroscientist 11:272-276.

Sutula T, Cascino G, Cavazos J, Parada I, Ramirez L (1989) Mossy fiber synaptic reorganization in the epileptic human temporal lobe. Ann Neurol 26:321-330.

Tauck D L, Nadler J V (1985) Evidence of functional mossy fiber sprouting in hippocampal formation of kainic acid-treated rats. J Neurosci 5:1016-1022.

Thomas A M, Corona-Morales A A, Ferraguti F, Capogna M (2005) Sprouting of mossy fibers and presynaptic inhibition by group II metabotropic glutamate receptors in pilocarpine-treated rat hippocampal slice cultures. Neuroscience 131:303-320.

Turski W A, Cavalheiro E A, Bortolotto Z A, Mello L M, Schwarz M, Turski L (1984) Seizures produced by pilocarpine in mice: a behavioral, electroencephalographic and morphological analysis. Brain Res 321:237-253.

Zhang W, St-Gelais F, Grabner C P, Trinidad J C, Sumioka A, Morimoto-Tomita M, Kim K S, Straub C, Burlingame A L, Howe J R, Tomita S (2009) A transmembrane accessory subunit that modulates kainate-type glutamate receptors. Neuron 61:385-396.

Zimmer J, Gahwiler B H (1984) Cellular and connective organization of slice cultures of the rat hippocampus and fascia dentata. J Comp Neurol 228:432-446.

The invention claimed is:

1. A method for treating or preventing epilepsy in a subject in need thereof, comprising
administering to the subject a therapeutically effective amount of a compound which is an antagonist of the GluK2/GluK5 receptor, wherein the compound is UBP310.

2. A method for treating or preventing epilepsy in a subject in need thereof, comprising
administering to the subject a therapeutically effective amount of a compound which is an antagonist of the GluK2/GluK5 receptor or an inhibitor of GluK2/GluK5 receptor expression, wherein the epilepsy is a temporal lobe epilepsy.

3. A method for treating or preventing epilepsy in a subject in need thereof, comprising
administering to the subject a therapeutically effective amount of a compound which is an antagonist of the GluK2/GluK5 receptor or an inhibitor of GluK2/GluK5 receptor expression, wherein the epilepsy is a chronic epilepsy.

* * * * *